(12) United States Patent
Hata et al.

(10) Patent No.: US 11,058,404 B2
(45) Date of Patent: Jul. 13, 2021

(54) LIQUID TEST DEVICE

(71) Applicant: Echo Electricity Co., Ltd., Fukushima (JP)

(72) Inventors: Hideaki Hata, Date-gun (JP); Ryozo Shiono, Date-gun (JP)

(73) Assignee: Echo Electricity Co., Ltd., Date-gun (JP)

( * ) Notice: Subject to any disclaimer, the term of this patent is extended or adjusted under 35 U.S.C. 154(b) by 690 days.

(21) Appl. No.: 14/888,126

(22) PCT Filed: Apr. 11, 2014

(86) PCT No.: PCT/JP2014/060502
§ 371 (c)(1),
(2) Date: Oct. 30, 2015

(87) PCT Pub. No.: WO2014/178274
PCT Pub. Date: Nov. 6, 2014

(65) Prior Publication Data
US 2016/0074019 A1   Mar. 17, 2016

(30) Foreign Application Priority Data

May 2, 2013   (WO) .................. PCT/JP2013/062789

(51) Int. Cl.
*A61B 10/00* (2006.01)
*A61B 3/10* (2006.01)
(Continued)

(52) U.S. Cl.
CPC ............ *A61B 10/0045* (2013.01); *A61B 3/10* (2013.01); *A61B 3/101* (2013.01); *A61B 5/4277* (2013.01);
(Continued)

(58) Field of Classification Search
None
See application file for complete search history.

(56) References Cited

U.S. PATENT DOCUMENTS 3,811,840 A * 5/1974 Bauer .................. C12Q 1/54
422/407
4,635,488 A * 1/1987 Kremer ............. A61B 10/0045
422/500
(Continued)

FOREIGN PATENT DOCUMENTS

JP    63-120605 U    8/1988
JP    2-1211 A      1/1990
(Continued)

*Primary Examiner* — Patrick Fernandes
*Assistant Examiner* — Benjamin S Melhus
(74) *Attorney, Agent, or Firm* — Westerman, Hatton, Daniels & Adrian, LLP

(57) ABSTRACT

A liquid test device has a liquid absorbing body 15; and a hydrophobic retaining body 20 that adheres tightly to the periphery of the liquid absorbing body 15 and cylindrically surrounds it. The liquid absorbing body 15 is formed into a shape of a long band having predetermined thickness and width, and the retaining body 20 includes a retaining base 11 that covers one face of the liquid absorbing body 15, a surface cover 19 that covers the other face of the liquid absorbing body 15, and side parts 13 that cover both sides of the liquid absorbing body 15. A liquid contact part 10e is provided at an end of the retaining body 20, an opening 23 for allowing the liquid absorbing body 15 to communicate with outside is provided on the retaining base 11 or the surface cover 19.

13 Claims, 21 Drawing Sheets

(51) Int. Cl.
*A61B 5/00* (2006.01)
*G01N 1/12* (2006.01)
*G01N 33/50* (2006.01)

(52) U.S. Cl.
CPC ............... *G01N 1/12* (2013.01); *G01N 33/50* (2013.01); *A61B 2562/0295* (2013.01)

(56) References Cited

U.S. PATENT DOCUMENTS

| | | | | |
|---|---|---|---|---|
| 4,857,453 A * | 8/1989 | Ullman | ............ | G01N 33/54366 435/7.92 |
| 5,006,310 A * | 4/1991 | Gin | ........................ | A61B 3/101 422/400 |
| 5,046,507 A * | 9/1991 | Nagase | .................. | A61B 3/101 600/558 |
| 5,135,873 A * | 8/1992 | Patel | ..................... | B01L 3/5023 422/412 |
| 5,170,799 A * | 12/1992 | Nagase | .............. | A61B 10/0045 128/897 |
| 5,260,031 A * | 11/1993 | Seymour | ................ | A61B 5/411 422/419 |
| 5,376,337 A * | 12/1994 | Seymour | ............ | A61B 10/0051 422/401 |
| 5,380,492 A * | 1/1995 | Seymour | ............ | A61B 10/0051 422/401 |
| 5,494,646 A * | 2/1996 | Seymour | ................ | A61B 5/411 422/401 |
| 5,602,040 A * | 2/1997 | May | ................ | G01N 33/54366 422/401 |
| 6,267,722 B1 * | 7/2001 | Anderson | ............ | G01N 21/474 600/300 |
| 6,316,205 B1 * | 11/2001 | Guan | .................. | G01N 33/558 422/401 |
| 6,653,066 B1 * | 11/2003 | Krutzik | ................ | G01N 33/558 423/55 |
| 6,840,911 B2 * | 1/2005 | Sangha | ............... | A61B 10/0051 422/412 |
| 7,133,712 B2 * | 11/2006 | Cohan | .................. | A61B 5/1486 600/345 |
| 7,192,555 B2 * | 3/2007 | Mink | .................. | A61B 10/0051 422/412 |
| 7,378,054 B2 * | 5/2008 | Karmali | ............. | A61B 10/0096 422/410 |
| 7,846,745 B2 * | 12/2010 | Saito | ..................... | G01N 33/558 436/514 |
| 8,647,890 B2 * | 2/2014 | Aberl | .................... | G01N 33/558 436/514 |
| 9,101,927 B2 * | 8/2015 | Alajem | ............... | B01L 3/5027 |
| 9,199,232 B2 * | 12/2015 | Flavin | .................. | B01L 3/5023 |
| 10,004,482 B2 * | 6/2018 | Roy | ................. | A61B 10/0045 |
| 2002/0102739 A1 * | 8/2002 | Nomura | ................. | G01N 1/30 436/169 |
| 2005/0013731 A1 * | 1/2005 | Burke | .................. | G01N 33/558 422/400 |
| 2005/0019212 A1 * | 1/2005 | Bhullar | ............. | G01N 27/3272 422/400 |
| 2006/0188410 A1 * | 8/2006 | Ishida | ................ | A61B 10/0051 422/400 |
| 2007/0048224 A1 * | 3/2007 | Howell | ................ | A61B 5/4277 424/9.1 |
| 2007/0278097 A1 * | 12/2007 | Bhullar | .................. | B23K 26/24 204/403.01 |
| 2008/0255474 A1 * | 10/2008 | Ishida | .................... | A61B 3/101 600/584 |

FOREIGN PATENT DOCUMENTS

| | | |
|---|---|---|
| JP | 2001-201437 A | 7/2001 |
| JP | 2005-253700 A | 9/2005 |
| JP | 2006-258773 A | 9/2006 |
| JP | 2008-259590 A | 10/2008 |
| JP | 2009-264988 A | 11/2009 |
| WO | 2012/080479 A1 | 6/2012 |

* cited by examiner

LIQUID TEST DEVICE

TECHNICAL FIELD

The present invention relates to a liquid test device that is made to contact and absorb a subject's liquid to be inspected, thereby performing inspection.

BACKGROUND ART

As conventional liquid test devices, tear meniscus test devices for measuring the amount of tear of a subject have been proposed in the following Patent Literatures 1 and 2, for example. The tear meniscus test device in Patent Literature 1 has a narrow and long hydrophilic member, and a groove extending in a longitudinal direction is provided to this hydrophilic member. The tear meniscus test device in Patent Literature 2 has a groove in its main body made of a synthetic resin or synthetic rubber material, and a hydrophilic member is placed in this groove.

With the test devices in the above Patent Literatures 1 and 2, the hydrophilic member is made to absorb tear by allowing an end of the device to contact tear meniscus, and by measuring the position the liquid has reached, the amount of tear is detected. According to this test device, it is possible to shorten the inspection time significantly, compared to conventional tests such as Schirmer's test.

The following Patent Literature 3 proposes a kit for diagnosing xerostomia of a subject. With this xerostomia diagnosing kit, filter paper for diagnosing xerostomia is prepared by embedding a reagent composition piece for inspection, which is filter paper impregnated with potassium iodide and starch in advance, in holes of another piece of filter paper. An end of this filter paper for diagnosing xerostomia is inserted into a mouth to make it absorb saliva, it is then taken out of the mouth after a predetermined period of time, a coloring reagent is applied, and the amount of production of saliva is inspected based on the degree of color development. The amount of production of saliva can thus be inspected by a simple method and in a relatively short time.

Patent Literature 4 proposes a thread for testing tear using a silicone tube with a scale. With this tear test device, a 0.2 mm-dia. cotton thread is made to pass through a silicone tube having inner diameter of 0.6 mm, for example, and an end of the cotton thread is made to protrude by 10 mm and fastened. To use it, the end of the cotton thread is inserted into a conjunctival sac and the length of liquid contact part is measured.

Patent Literature 5 proposes a biological liquid sampling tool for analyzing the composition of the liquid sampled. This biological liquid sampling tool includes: a base sheet having a through hole and a slit communicating with the through hole and opening externally; two cover sheets laminated on both sides of the base sheet; and a liquid absorbing body placed in the opening slit between the cover sheets. This biological liquid sampling tool ensures short sampling time by capitalizing on capillarity of a short liquid absorbing body having a small absorption volume. Furthermore, by disposing the absorbing body at the sampling port, thereby minimizing the path length, a biological liquid of small abundance can be extracted.

CITATION LIST

Patent Literature

Patent Literature 1; JP 2005-253700 A
Patent Literature 2; JP 2008-259590 A
Patent Literature 3; JP 2009-264988 A
Patent Literature 4; JP 1988-120605 U
Patent Literature 5; JP 2006-258773 A

SUMMARY OF INVENTION

Solution to Problem

However, the test devices disclosed in the above Patent Literatures 1 to 3 have a structure where the surface of the hydrophilic member and the filter paper is exposed, allowing oil component to attach to the hydrophilic member and the filter paper at the time of manufacture or transportation. Fingers thus directly contact the hydrophilic member and the filter paper when the device is used, and the amount of absorption and absorption speed may have varied due to attachment of oil content, etc. of fingers. In particular, when a small amount of target liquid is inspected, inspection time and accuracy were affected significantly. Furthermore, since the surface of the hydrophilic member and the filter paper is exposed, there is a possibility that the amount of absorption varies because the degree of swelling of the hydrophilic member at the time of absorption is not uniform.

Since the tear test device in the above Patent Literature 4 has the structure where the cotton thread having a diameter of approximately ⅓ of the inner diameter of the silicone tube is inserted, despite that the cotton thread is covered by the silicone tube, it is essential to ensure inspection time appropriate to the absorption speed of the cotton thread. In addition, if the shape of the cotton thread varies and the liquid to be inspected is stored in a space between the cotton thread and the silicone tube, an error is caused in the surface level of the absorbed liquid to be inspected. Since the above Patent Literature 5 has the structure where the short liquid absorbing body is placed near the sampling port, thereby absorbing the liquid to be inspected in a short time, a trace amount of liquid to be inspected cannot be measured with high accuracy.

A purpose of the present invention is to provide a liquid test device that can perform inspection with high accuracy and in a short inspection time.

Means for Solving the Problems

A liquid test device of the present invention to achieve the above objective comprises: a liquid absorbing body; and a hydrophobic retaining body for retaining the liquid absorbing body by adhering tightly to and cylindrically surrounding the periphery of the liquid absorbing body wherein the liquid absorbing body is formed in a shape of a long band having predetermined thickness and width, and the retaining body includes: a retaining base for covering one face of the liquid absorbing body; a surface cover for covering the other face of the liquid absorbing body; and side parts that cover both sides of the liquid absorbing body. At an end of the retaining body, a liquid contact part created by exposing an end of the liquid absorbing body is provided. At a position of the retaining base or the surface cover, or of both, apart from the liquid contact part, an opening for allowing the liquid absorbing body to communicate with outside is provided, and a scale for measuring the amount of liquid absorbed by the liquid absorbing body is provided between the liquid contact part and the opening.

The opening of this liquid test device preferably is a cut or opening formed at a position of the retaining base or the surface cover, or of both, corresponding to the liquid absorbing body. A plurality of liquid absorbing bodies may be provided via an isolating part of the retaining body, and each of the plurality of liquid absorbing bodies may be exposed as different liquid contact parts. In that case, it is desirable that liquid contact parts be provided on both ends of the longitudinal direction of the retaining body, and that identifying parts for allowing one and the other liquid contact parts to correspond to one and the other inspection objects be provided in the retaining body. As the identifying parts, a plurality of openings having shapes different from one another may be formed at different positions.

This liquid test device may be constituted by a band-shaped main body equipped with the liquid absorbing body and the retaining body, and the liquid contact part protruding from one end of this main body. One face or both faces of this liquid contact part may be supported by the retaining body.

Advantageous Effect of the Invention

According to the liquid test device of the present invention, the periphery of the band-shaped liquid absorbing body is adhered tightly to and cylindrically surrounded by the retaining body, the liquid contact part formed by exposing an end of the liquid absorbing body is provided at an end of the retaining body, and the opening for allowing the liquid absorbing body to communicate with outside is provided at a position of the retaining base or the surface cover, or of both, apart from the liquid contact part. When a liquid to be inspected is made to contact the liquid contact part, the liquid is absorbed by the liquid absorbing body by capillary action. Since the liquid absorbing body is cylindrically surrounded by the retaining body, fingers are not allowed to directly touch the liquid absorbing body, and thus unlike prior art, absorption of the liquid cannot be inhibited by oil or dust having attached to the liquid absorbing body.

Furthermore, despite that the band-shaped liquid absorbing body is cylindrically surrounded by the retaining body, the liquid absorbing body is communicating with outside at the opening that is apart from the liquid contact part. Consequently, when the liquid absorbing body absorbs the liquid to be inspected, an air existing within the liquid absorbing body can be discharged from the opening, thereby preventing the speed of liquid absorption from decreasing due to the air existing inside. It is therefore possible to absorb and measure the liquid in a short time. Inspection time can thus be shortened.

The liquid absorbing body is formed in a shape of a long band having predetermined thickness and width so that the thickness and width are preferably maintained constant in the longitudinal direction, and the periphery of this liquid absorbing body is adhered tightly to and cylindrically surrounded by the retaining body. Consequently, when the liquid absorbing body absorbs the liquid to be inspected, the liquid is not allowed to be absorbed by the retaining body. The absorbed liquid cannot attach to the surface of the liquid absorbing body excessively, or absorbed liquid cannot swell excessively but the liquid surface is made to be displaced in proportion to the amount of liquid absorbed with high accuracy. Furthermore, since the liquid absorbing body is in a shape of a long band, displacement of the liquid surface is large when the liquid is absorbed, meaning that even a small amount of liquid can be inspected with high accuracy in a short time.

In addition, if the liquid contact part of this liquid test device is provided, protruding from the main body, the area that contacts the liquid to be inspected can be increased, thereby facilitating absorption of the liquid by the liquid absorbing body. The liquid can thus be absorbed and measured in a shorter time.

DESCRIPTION OF EMBODIMENTS

The present invention will hereinafter be descried in detail by referring to some embodiments and using the drawings.

First Embodiment

Figure 1:
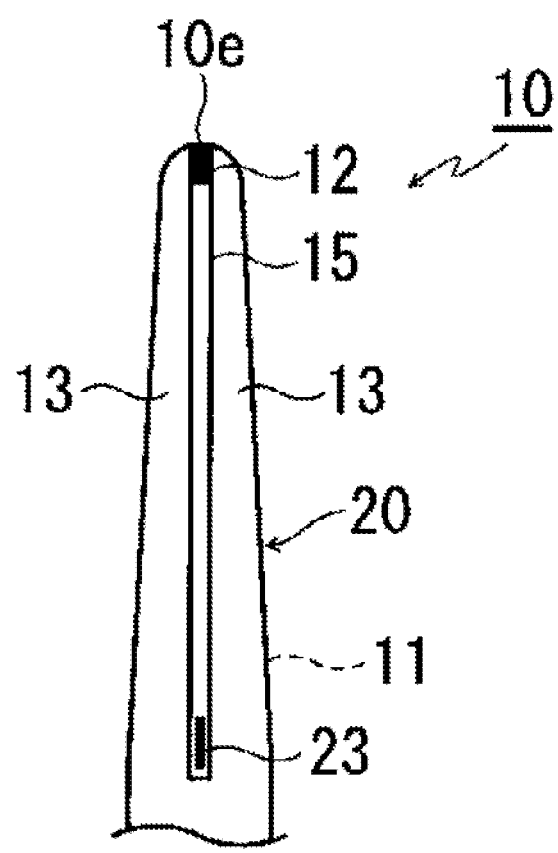
FIG. 1 is a front view showing a part of a liquid test device according to a first embodiment of the present invention.
Figure 2:
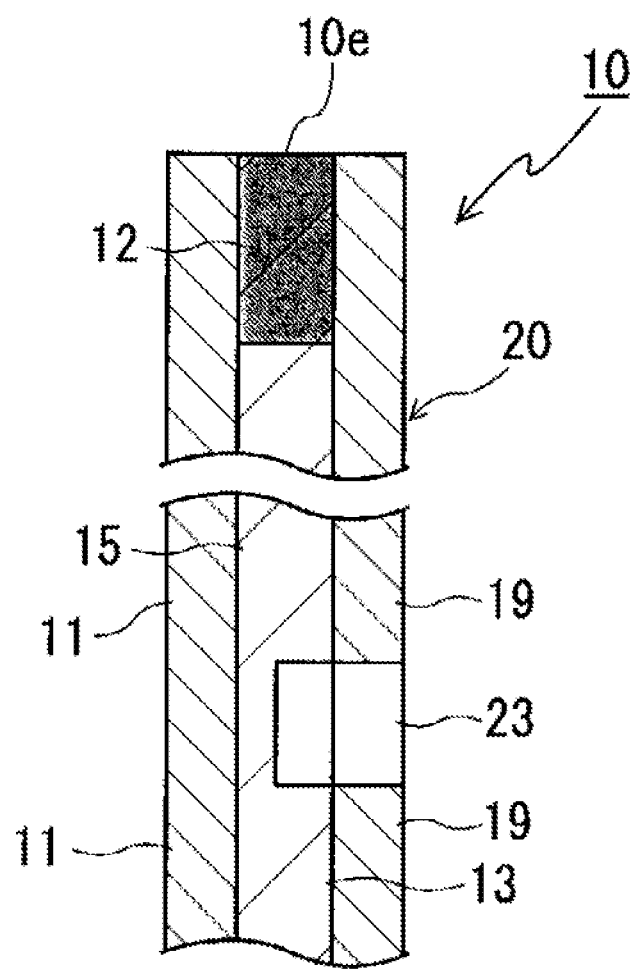
FIG. 2 is a cross-sectional view in a vertical direction of the liquid test device according to the first embodiment of the present invention.
Figure 3:
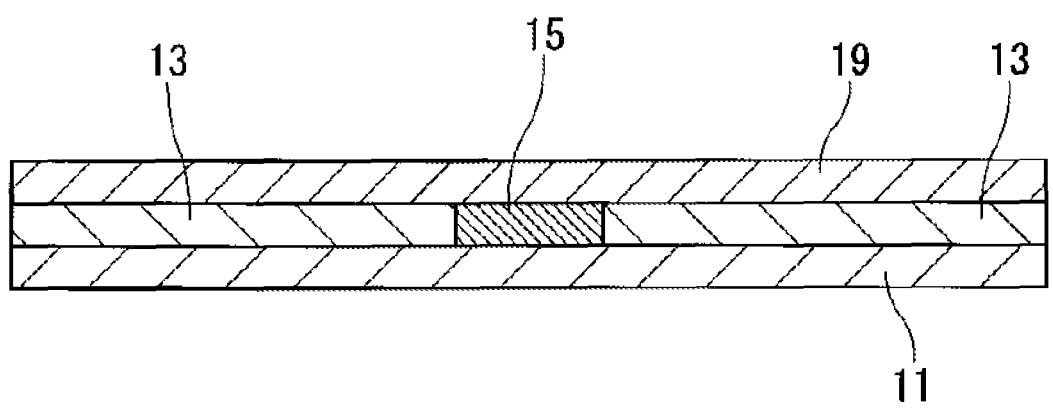
FIG. 3 is a cross-sectional view in a horizontal direction of the liquid test device according to the first embodiment of the present invention.

This embodiment is an example of a tear meniscus measuring device. As shown in FIGS. 1 to 3, a liquid test device 10 of the present invention comprises: a liquid absorbing body 15, which is in a shape of a thin plate extending longitudinally in a direction of an axis, and has a band-shaped hydrophilic property; and a hydrophobic retaining body 20 for adhering tightly to and cylindrically surrounding the liquid absorbing body 15. The hydrophilic property in this case is interpreted as the property of absorbing a liquid not only superficially but also down into the material, and the hydrophobic property means the property of not absorbing a liquid as far as possible.

At an end of the liquid test device 10 in a longitudinal direction, a liquid contact part 10e that is made to contact a liquid to be inspected is provided. This liquid contact part 10e is formed by exposing an end of the liquid absorbing body 15 from an end of the retaining body 20 to outside. At a position apart from the liquid contact part 10e, an opening 23 that communicates with outside is provided by exposing the liquid absorbing body 15 from the retaining body 20. The liquid contact part 10e is formed in an arc shape in front view, and the end of the retaining body 20 and that of the liquid absorbing body 15 are arranged to be laminated in the same shape.

The liquid absorbing body 15 is formed in a shape of a long band having smaller width and length than those of the retaining body 20, and fastened to the retaining body 20 along the longitudinal direction. In this example, the liquid absorbing body 15 is formed so that it has a constant width and thickness along mostly the whole length. The liquid absorbing body 15 has hydrophilic property, meaning that it can absorb a liquid to be inspected when the liquid is made to contact the liquid contact part 10e. Absorption may be allowed to occur, for example, by surface tension that builds up as a result of contact of the liquid to be inspected to the liquid absorbing body 15. It is desirable that a material highly compatible with the liquid to be inspected be selected for the liquid absorbing body 15. To prevent damage of the retaining body 20 when it is deformed, it is preferable to use a flexible material.

As materials for the liquid absorbing body 15, various resins, fibers such as rayon or pulp, woven cloth, nonwoven cloth, paper, etc. may be used for example. It is desirable that the material have many minute voids inside to allow the liquid to be absorbed. A material having a void ratio of 50% to 95% may be used for example. If the void ratio is excessively high, the shape of the liquid absorbing body 15 cannot be maintained stably, causing error to occur easily at the time of measurement. Meanwhile if the ratio is excessively low, the amount of liquid per unit length becomes small when the liquid is absorbed, causing the length of the liquid test device 10 to be longer. As a material for the liquid absorbing body 15, a material having weighing capacity of 30 g/m$^2$ to 100 g/m$^2$ may be used, and the one having density of 0.05 to 0.3 g/cm$^3$ may also be used.

The liquid absorbing body 15 has a width, a thickness, and a length allowing a desired amount of liquid to be absorbed in a desired range when the liquid is absorbed. In this embodiment, the liquid absorbing body 15 is formed in mostly constant thickness and width over mostly the entire length in a longitudinal direction. Consequently, when the liquid is absorbed, the liquid level of the liquid absorbing body 15 can be displaced with high accuracy in proportion to the amount of liquid absorbed. The thickness, the width, and the length of the liquid absorbing body 15 can be set depending on the material of the liquid absorbing body 15, amount of liquid, etc. For example, when the amount of liquid to be absorbed in each inspection falls within a range from 0.2 μL to 5 μL, its cross section can be set to be 0.1 to 0.5 mm$^2$, its length to be 20 to 60 mm, and its thickness to be 0.15 to 0.5 mm.

It is desirable that the liquid absorbing body 15 be adhered tightly to the retaining body 20 without a gap over the entire periphery. If there is a gap between the liquid absorbing body 15 and the retaining body 20, absorbed liquid may be placed in that gap, thereby easily causing error to occur in the liquid level with respect to the mount of liquid absorbed.

A material having fast absorbing speed is used for the liquid absorbing body 15. The liquid absorbing speed can be measured as follows: a strap-shaped test piece having the same thickness as the liquid absorbing body 15 is created using the material constituting the liquid absorbing body 15; this test piece is placed by itself in a vertical direction, the bottom end of the test piece is immersed by 0.1 mm to 3 mm in a sufficient amount of stored liquid to be inspected for 5 seconds; and a distance between the highest position of the absorbed liquid and the level of the liquid to be inspected is measured. It is desirable that such absorbing speed be 1 mm/sec. or higher, and more preferably 3 mm/sec. or higher. Since the entire length of the obtained liquid test device becomes long if the speed is excessively high, it should be 30 mm/sec. or lower for example, and more preferably 20 mm/sec. or lower.

The suction force may be improved by providing a slit or a plurality of slits extending in a longitudinal direction on the surface of the liquid absorbing body 15. The slit may be a mere cut, a V-shaped groove, or a semicircular groove. The higher the number of slits, the higher the liquid suction force by surface tension.

The liquid absorbing body 15 or the retaining body 20 that contacts the liquid absorbing body 15 is provided with a coloring indicator 12 for improving visibility of the liquid and liquid interface absorbed by the liquid absorbing body 15. The indicator can change the color of the liquid absorbing body 15 when it contacts the liquid to be inspected.

The coloring indictor 12 is made of a dissolvable or dispersible dye, etc. depending on the liquid to be inspected. In the case of a liquid test device 10 used by contacting human body, such as the one used to check dry mouth or dry eye, it is desirable to use blue No. 1 (brilliant blue FCF), etc. This coloring indicator 12 is adhered to and infiltrated into an end of the liquid absorbing body 15 placed in the liquid contact part 10e. An arbitrary method of partially attaching the coloring indicator 12 may be selected. For example, a line crossing the liquid absorbing body 15 may be formed by printing etc., or dots may also be formed.

In this embodiment, as another coloring indicator 12, the entire liquid absorbing body 15 is impregnated with a pH indicator to allow pH to be measured while the liquid is inspected. The pH indicator can be selected as required according to the liquid to be inspected. With tear for example, phenol red, etc. can be used. The method to impregnate the liquid absorbing body 15 with a pH indicator is not limited. For example, the liquid absorbing body 15 may be impregnated with a solution containing a pH indicator and dried.

The retaining body 20 includes a hydrophobic retaining base 11 formed in a shape of a thin band to cover the rear face of the liquid absorbing body 15, hydrophobic side parts 13 that are fastened to the surface side of the retaining base 11 and cover both sides of the liquid absorbing body 15, and surface cover 19 that are fastened to the surface side of the retaining base 11 and surface side of the side parts 13 and cover the surface of the liquid retaining body 15.

The retaining base 11 is formed in a size larger than that of the liquid absorbing body 15, and fastens the rear side of the liquid absorbing body 15. The retaining base 11 is made of a hydrophobic sheet, film, tape, etc. that does not absorb the liquid to be inspected inside. A material having an adhesive on one side may also be used. When the hydrophobic material is used as the retaining base 11, the amount of liquid to be absorbed by the retaining base 11 can be suppressed as little as possible, thereby minimizing measurement error. In this embodiment, the same material as the surface cover 19, which will be described later, is used.

The side parts 13 are placed continuously in a longitudinal direction so that they contact the entire length of the liquid absorbing body 15 on both sides, and adhered tightly to and fastened to the surface of the retaining base 11 over mostly the entire length on the rear side. The side parts 13 may be formed into one piece with the retaining base 11. These side parts 13 reinforce the retaining base 11 and the liquid absorbing body 15 and prevent the liquid having been absorbed into the liquid absorbing body 15 from being dispersed toward the sides of the liquid absorbing body 15. The side parts 13 are made of the hydrophobic material as in the case of the retaining base 11, a urethane film for example. In this embodiment, to measure the amount of liquid having been absorbed by the liquid absorbing body 15, a scale 21 of various types is printed on the side parts 13 between the liquid contact part 10*e* and the opening 23. It is only necessary that the scale 21 is provided in at least a part between the liquid contact part 10*e* and the opening 23. In this embodiment, the scale 21 is provided over the entire length between the liquid contact part 10*e* and the opening 23.

The surface cover 19 is adhered to the liquid absorbing body 15 and side parts 13 to cover the surface of both to protect them. Mostly the entire part of the surface cover 19 is adhered tightly to and fastened to the surface of the liquid absorbing body 15 and the side parts 13. By sandwiching the liquid absorbing body 15 between the retaining base 11 and the surface cover 19, the liquid absorbing body 15 is fastened while its thickness is being compressed. In this embodiment, the compressed liquid absorbing body 15 has the same thickness as the side parts 13.

The surface cover 19 is made of the hydrophobic sheet, film, tape, etc. that do not absorb the liquid to be inspected inside. A material having an adhesive on one side may also be used. By using the hydrophobic material as the surface cover 19, the amount of the liquid absorbed by the surface cover 19 can be suppressed to as little as possible, thereby decreasing measurement error. It is desirable that this surface cover 19 have transparency of a degree allowing the scale 21, a coloring indicator 12, a pH indicator, etc. to be recognized visually. It is especially preferable that it is transparent enough for the liquid absorbed by the liquid absorbing body 15 to be recognized visually.

With this liquid test device 10, as shown in FIG. 3, the liquid absorbing body 15 is surrounded by and adhered tightly to the retaining base 11, a pair of side parts 13, and the surface cover 19. An end of this liquid absorbing body 15 is exposed to outside by being placed at the liquid contact part 10*e*. Meanwhile, the other end of the liquid absorbing body 15 is placed in the middle of the retaining body 11, the pair of side parts 13, and the surface cover 19 in a longitudinal direction. At a position of the surface cover 19 corresponding to the other end of this liquid absorbing body 15, an opening 23 is provided. This opening 23 allows the liquid absorbing body 15 to communicate with outside. The opening 23 in this embodiment is a cut extending along the longitudinal direction of the liquid absorbing body 15. The cut may be allowed to pass through the surface cover 19 only. In this embodiment, however, the depth of the cut is set so that it passes through the surface cover 19 and reaches the inside of the liquid absorbing body 15.

A method of measuring a liquid to be inspected using the above liquid test device 10 will then be described. In this example, the amount of the liquid to be inspected is measured. Any liquids can be inspected, provided that they can be absorbed by the liquid absorbing body 15. For example, body liquids such as tear and saliva, various solutions, aqueous dispersion, non-aqueous liquids, etc. may also be measured. In this embodiment, tear meniscus is inspected.

First, an end of the liquid contact part 10*e* is allowed to contact the lower eyelid of one eye of a subject by holding the liquid test device 10. The tear is thus made to contact the liquid absorbing body 15 exposed to an end of the liquid test device 10, and absorbed by capillary action.

Once the tear having been absorbed contacts the coloring indicator 12, the coloring material of the coloring indicator is dissolved, absorbed by the liquid absorbing body 15 together with the tear, and liquid interface moves toward the other end. The amount corresponding to the amount of tear in the lower eyelid is absorbed by the liquid absorbing body 15, and the measurement is thus completed. The position the liquid interface of the liquid absorbing body 15 has reached at that time is checked visually from the surface side through the surface cover 19, and the amount of tear is measured using the scale 21. Also the pH of the tear is checked according to the color of the liquid absorbing body 15. The tear meniscus inspection of the subject is thus completed.

According to the liquid test device 10 described above, the periphery of the long band-shaped liquid absorbing body 15 is adhered tightly to and cylindrically surrounded by the retaining body 20. The liquid contact part 10*e* made by exposing the end of the liquid absorbing body 15 is provided at the end of the retaining body 20, and the opening 23 for allowing the liquid absorbing body 15 to communicate with outside is provided on the surface cover 19 at a position apart from the liquid contact part 10*e*. Consequently, when the liquid to be inspected is made to contact the liquid contact part 10*e*, the liquid is absorbed by the liquid absorbing body 15, and climbs up the liquid absorbing body 15 by the length corresponding to the amount of liquid by capillary action. Since the liquid absorbing body 15, which is cylindrically surrounded by the retaining body 20, does not directly contact fingers, the oil component does not attach to the liquid absorbing body 15 and thus the absorption of the liquid to be inspected cannot be inhibited, unlike conventional devices.

Furthermore, since the liquid absorbing body 15 communicates with outside at the opening 23 apart from the liquid contact part 10*e* despite that the liquid absorbing part 15 is cylindrically surrounded by the retaining body 20, the air existing within the liquid absorbing body 15 can be discharged from the opening 23 to prevent liquid absorption speed from decreasing due to the air existing inside. The liquid to be inspected can thus be absorbed and measured in a short time, and the inspection time can be shortened.

Since the thin liquid absorbing body 15 is in a structure cylindrically surrounded by the hydrophobic retaining body 20, the liquid having been made to contact the liquid contact part 10*e* is absorbed by the liquid absorbing body 15 only, and even the surface of a small amount of liquid can transfer to inside of the liquid test device 10. Furthermore, the liquid absorbing body 15 is formed in a shape of a long band having a predetermined thickness and width along the longitudinal direction, and the periphery of the liquid absorbing body 15 is adhered tightly to and cylindrically surrounded by the retaining body 20. Consequently, when the liquid absorbing body 15 absorbs the liquid to be inspected, the absorbed liquid does not attach to the surface of the liquid absorbing body 15 excessively, or swell excessively. The liquid surface can thus be displaced accurately in proportion to the amount of liquid absorbed. Furthermore, since the liquid absorbing body 15 is in a shape of a long band, the displacement of the liquid is large when the liquid is absorbed. Even a small amount of liquid to be inspected can thus be inspected in a short time and with high accuracy.

With this liquid test device 10, since the coloring indicator 12 is attached to the liquid absorbing body 15, the liquid absorbed by the liquid absorbing body 15 can be visually recognized easily as a result of contact of the liquid with the coloring indicator 12.

Since the opening 23 is formed as a cut extending in a longitudinal direction at a position of the surface cover 19 corresponding to the liquid absorbing body 15, the liquid absorbing body 15 can be made to communicate with outside in a shortest distance. Furthermore, the working volume can be suppressed, ensuring wide opening area of the liquid absorbing body 15. That is why the strength of the liquid test device 10 does not decrease excessively, and even if the width of the liquid test device 10 is made to be narrow, the device does not bend or deform around the opening 23 during use. Furthermore, since the cutting does not produce removed part at the time of processing, the manufacturing is facilitated.

The retaining body 20 is covered by a pair of side parts 13 on both edges of the liquid absorbing body 15. Since this pair of side parts 13 is inserted between the retaining base 11 and the surface cover 19, the thickness of the liquid absorbing body 15 can be maintained stable compared to the case where the retaining base 11 and the surface cover 19 are directly connected to each other. Measurement accuracy of the liquid to be inspected can thus be improved.

The embodiment described above can be modified as required within the scope of the present invention. For example, the retaining body 20 and the liquid absorbing body 15 may not necessarily be straight lines extending in an axial direction, but may be provided in a curved or bent state. Furthermore, although the case where a cut was formed as the opening 23 on the surface cover 19 was described above, the place of making a cut is not limited to the surface cover. The cut may be made on the retaining base 11.

Second Embodiment

Figure 4:
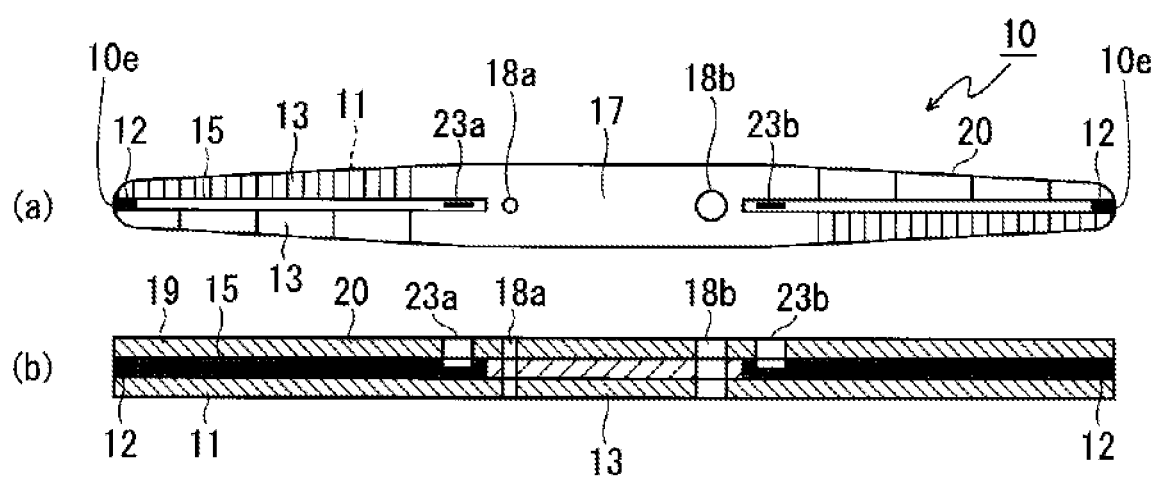
FIG. 4 shows a liquid test device according to a second embodiment of the present invention, where (a) is a front view, and (b) is a cross-sectional view in a vertical direction.

FIGS. 4 (*a*) and (*b*) show a liquid test device in a second embodiment. With the liquid test device 10 in this embodiment, liquid contact parts 10*e* are provided on both sides viewed from the front. In this example, two liquid absorbing bodies 15 are provided, and they are respectively exposed at respective liquid contact part 10*e*. The liquid absorbing body 15 at an end and that on the other end are formed in the same shape.

At an intermediate position between the liquid contact parts 10*e* on both ends, a separating part 17 is provided to separate the liquid absorbing body 15 on one end and the liquid absorbing body 15 on the other end. The separating part 17 makes the liquid absorbing body 15 on one end and the liquid absorbing body 15 on the other end discontinuous, and no liquid absorbing body 15 is placed in this separating part 17. Furthermore, in this embodiment, in order for the one liquid contact part 10*e* and the other liquid contact part 10*e* to respectively correspond to one and the other inspection targets, they are respectively provided with an identifying part 18*a*, 18*b* in different shapes. These identifying parts 18*a*, 18*b* can be formed by various methods such as printing, cutting, and punching, their shapes can be selected arbitrarily, and characters such as "R" and "L" may also be selected. In this embodiment, the identifying parts 18*a*, 18*b* are formed by through holes penetrating the retaining body 18. Specifically, the other identifying part 18*b* is formed larger than one identifying part 18*a*, with the diameter of the former visually identifiable to be larger. Each identifying part 18*a*, 18*b* is provided at a position displaced toward each end from the center of the isolating part 17 in the longitudinal direction. Other structures are the same as the first embodiment.

To measure a liquid to be inspected using the liquid test device 10 in the second embodiment, the inspection can be performed as in the case of the first embodiment by using one liquid contact part 10*e* and liquid absorbing body 15. Then the liquid test device 10 is reversed and held, and the inspection is performed by using the other liquid contact part 10*e* and liquid absorbing body 15. By allowing the liquid contact part 10*e* on the other end to contact the lower eyelid of the other eye and allowing tear to contact the liquid absorbing body 15 on the other side, the liquid is absorbed by capillary action. The absorbed tear contacts the coloring indicator 12, and the liquid interface transfers to the side of the separating part 17 together with the coloring material of the coloring indicator. The amount corresponding to the amount of tear is absorbed by the absorbing body 15, and the amount of tear is measured by checking the position the liquid interface has reached using the scale 21. By using a single liquid test device 10, inspection can be performed twice with one end and the other end of the device. By using a single liquid test device 10, liquid meniscus of both eyes of a subject can thus be measured.

The above liquid test device 10 can also provide the same functional effect as the first embodiment. Furthermore, with the liquid test device 10 in the second embodiment, since the two liquid absorbing bodies 15 are provided apart from each other and are respectively exposed at different openings 23*a*, 23*b* and liquid contact parts 10*e*, the measurement of liquid can be performed two or more times with just a single device. In addition, the liquid absorbed by the liquid absorbing body 15 on one end does not reach the other end even if a liquid absorbing body 15 having high liquid absorbing speed is used. Two or more inspections can thus be performed in a short time, which is quite convenient.

Also, since the identifying parts 18a, 18b formed in different shapes as two through holes are provided at different positions, by visually checking the positional relation of the two identifying parts 18a, 18b, the orientation of the liquid test device 10 can be assessed easily, and the liquid contact parts 10e on both ends can be easily distinguished from each other visually. Consequently, when testing the amount of liquids by sequentially using the liquid contact parts 10e at both ends, each liquid contact part 10e of the liquid test device 10 can be assigned to each eye instantaneously, which facilitates handling of the liquid test device 10 when used for inspections.

[Modification]

Figure 5:
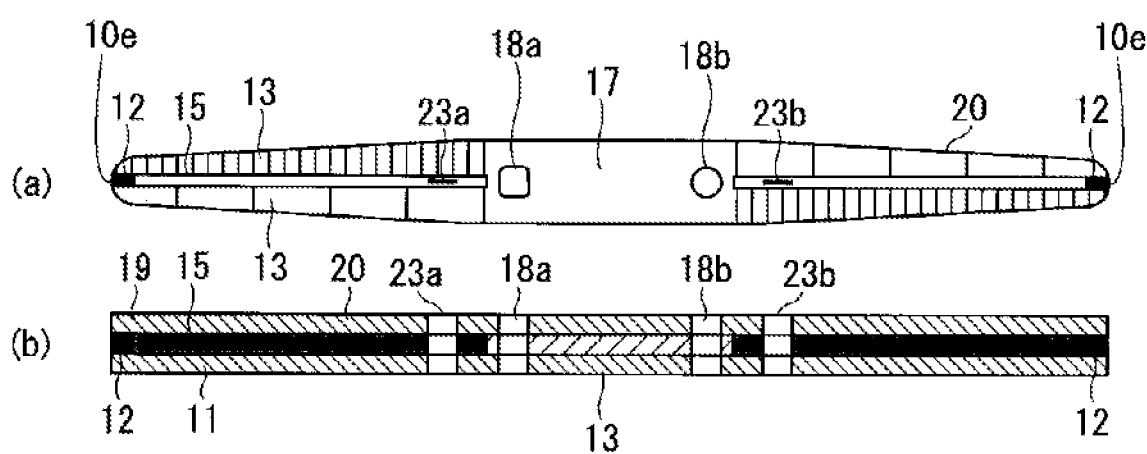
FIG. 5 shows a modification of the liquid test device according to the second embodiment of the present invention using an identifying part, where (a) is a front view, and (b) is a cross-sectional view in a vertical direction.

In the second embodiment described above, cuts are provided as openings 23a, 23b on the side of the surface cover 19. As shown in FIGS. 5 (a) and (b), however, cuts may be provided by penetrating the surface cover 19, liquid absorbing body 15, and retaining base 11. Furthermore, one of the identifying parts 18a, 18b may be formed in a different shape such as square, while the other may be formed into a circular form. The identifying parts 18a, 18b may be formed by thus combining shapes different from each other. Also, the scale 21 may be allowed to be longer than the distance between the liquid contact part 10e and the opening 23.

Figure 6:
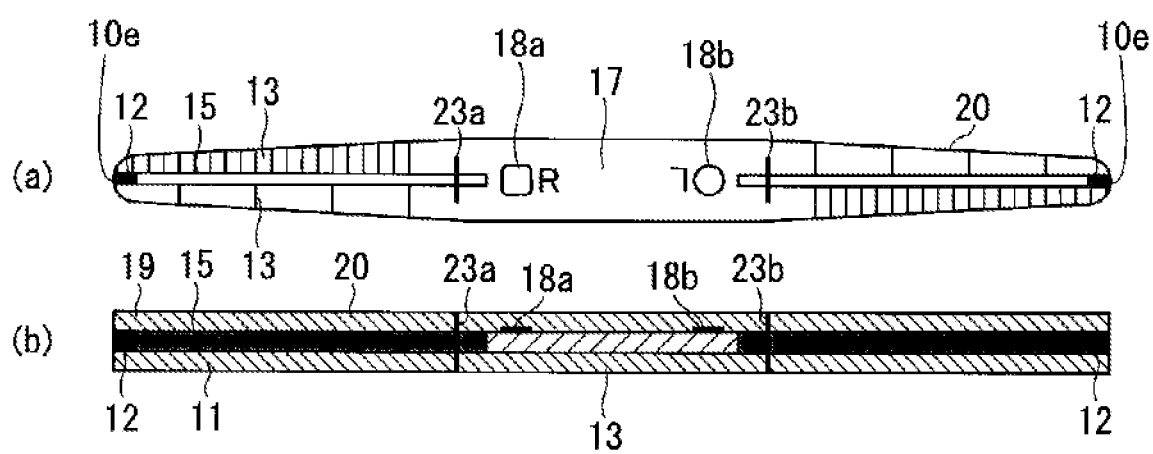
FIG. 6 shows a modification of the liquid test device according to the second embodiment of the present invention, with the orientation of a cut varied, where (a) is a front view, and (b) is a cross-sectional view in a vertical direction.

In the second embodiment described above, the identifying parts 18a, 18b are formed as through holes. It is also possible to display the identifying parts 18a, 18b by printing at positions visible from outside of the side parts 13, retaining base 11, and surface cover 19. Their shapes and quantity may be selected arbitrarily. As shown in FIGS. 6 (a) and (b), figures in different shapes and characters such as "R" and "L" may be formed by printing. It is also possible to provide openings 23a, 23b in a direction crossing the longitudinal direction, as shown in FIGS. 6 (a) and (b).

Figure 7:
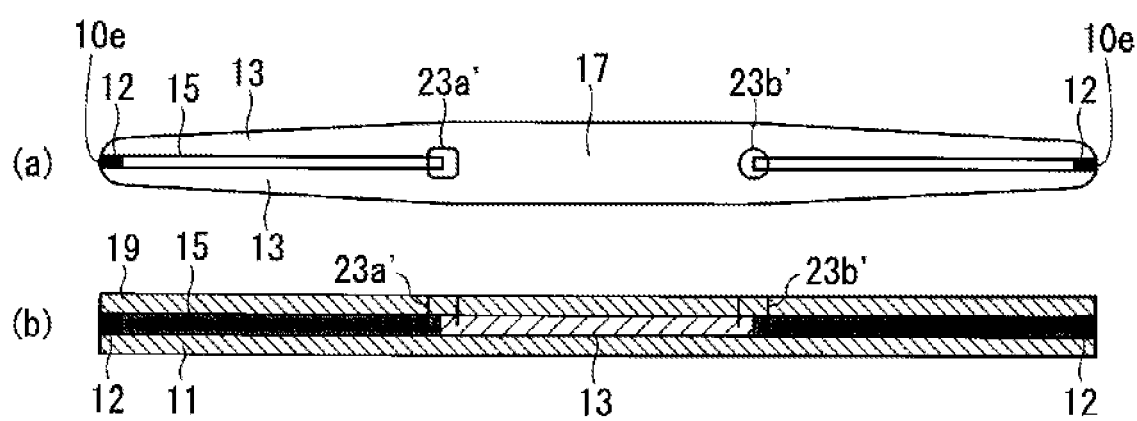
FIG. 7 shows a modification of the liquid test device according to the second embodiment of the present invention, with the shape of the cut varied, where (a) is a front view, and (b) is a cross-sectional view in a vertical direction.

As shown in FIG. 7, the openings 23a, 23b can also be formed by creating cuts in a polyangular shape 23a' and a circular shape 23b'. In that case, by allowing the shape of the openings 23a', 23b' to be visible, they can be used as substitutes of identifying parts 18a, 18b.

Figure 8:
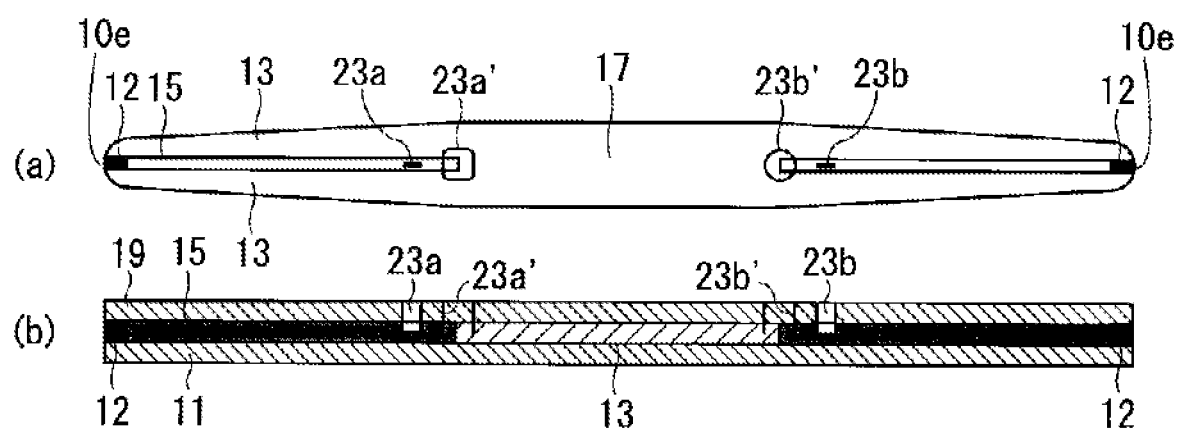
FIG. 8 is a modification of the liquid test device according to the second embodiment of the present invention where a plurality of cuts are provided, where (a) is a front view, and (b) is a cross-sectional view in a vertical direction.

Furthermore, as shown in FIGS. 8 (a) and (b), linearly cut openings 23a, 23b may be formed together with the openings 23a', 23b'.

Figure 9:
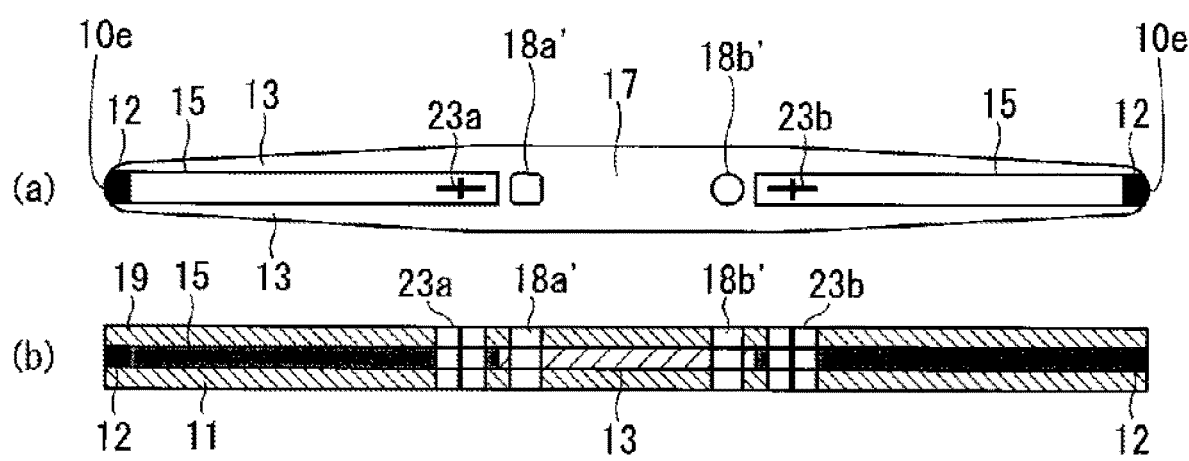
FIG. 9 shows a modification of the liquid test device according to the second embodiment of the present invention where a plurality of cuts are provided crossing each other, where (a) is a front view, and (b) is a cross-sectional view in a vertical direction.

As shown in FIGS. 9 (a) and (b), the openings 23a, 23b may also be provided by forming a linear cut extending in the longitudinal direction of the liquid absorbing body 15 and a linear cut shorter than the width of the liquid absorbing body 15 so that they cross each other.

Third Embodiment

Figure 10:
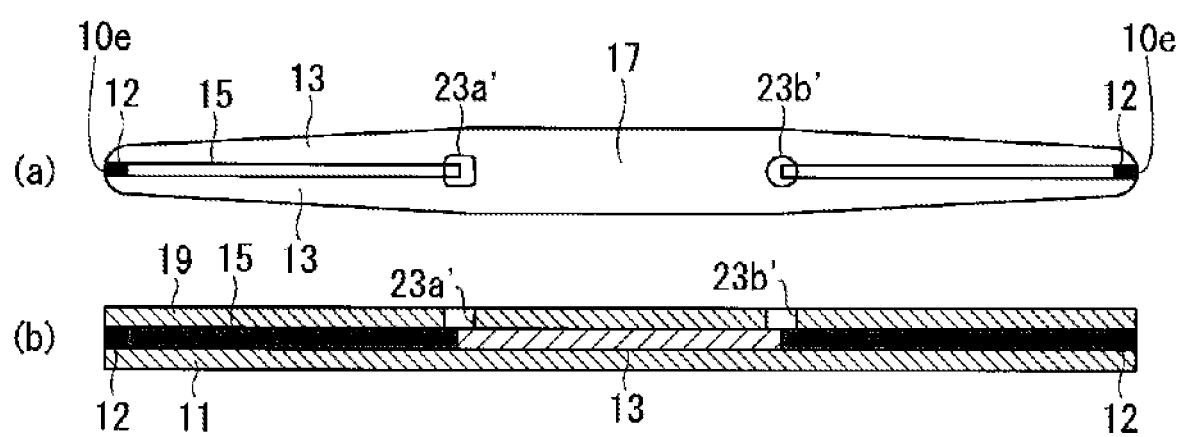
FIG. 10 shows a liquid test device according to a third embodiment, where (a) is a front view, and (b) is a cross-sectional view in a vertical direction.

FIGS. 10 (a) and (b) show a liquid test device in a third embodiment. With the liquid test device 10 in this embodiment, openings 23a', 23' are formed as holes. This embodiment is the same as the second embodiment except that the opening 23a' is in a polygonal shape such as square, and opening 23b' is in a circular shape, created on the surface cover 19.

This liquid test device 10 can also provide the same functional effect as the second embodiment. Furthermore, with this liquid test device 10, openings 23a', 23b are created as holes, and furthermore their shapes are different from each other. Consequently, it is easy to identify the orientation of the liquid test device 10 as in the case of identifying parts 18a, 18b.

[Modification]

Figure 11:
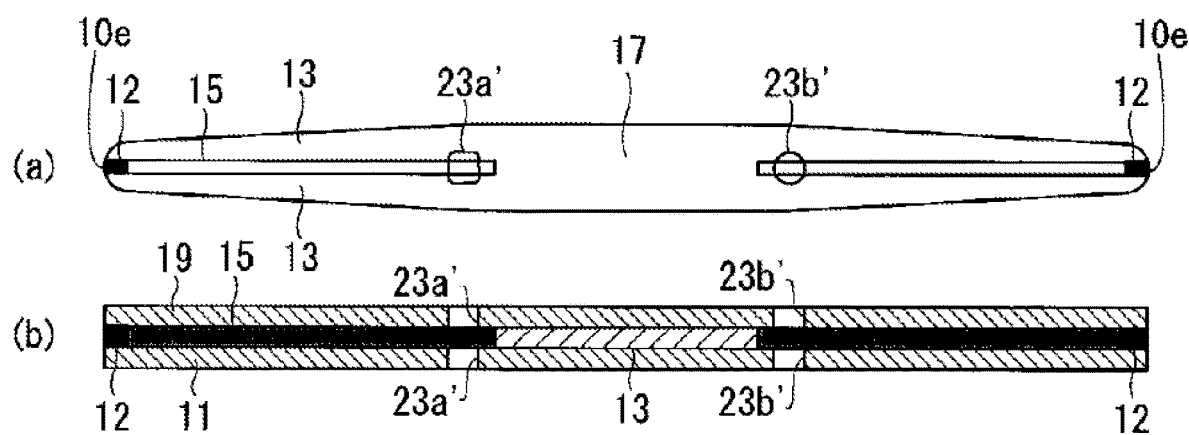
FIG. 11 shows a modification of the liquid test device according to the third embodiment with openings provided on both faces, where (a) is a front view, and (b) is a cross-sectional view in a vertical direction.

In the third embodiment described above, openings 23a', 23b' are provided on the surface cover 19. However, the openings 23a', 23b' may be formed on the retaining base 11. It is also possible to provide the openings 23a', 23b' on both the surface cover 19 and the retaining base 11 as shown in FIGS. 11 (a) and (b).

Fourth Embodiment

Figure 12:
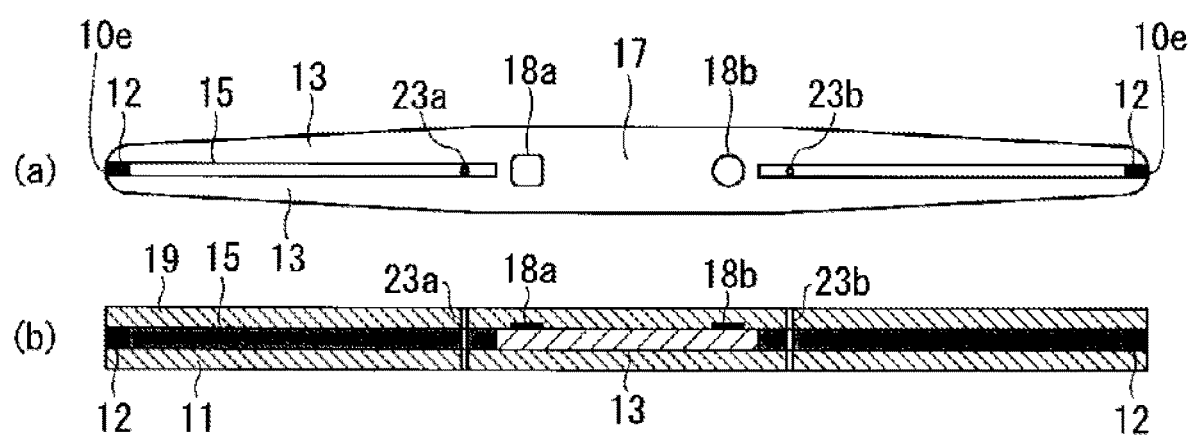
FIG. 12 shows a liquid test device according to a fourth embodiment of the present invention, where (a) is a front view, and (b) is a cross-sectional view in a vertical direction.

FIGS. 12 (a) and (b) show a liquid test device in a fourth embodiment. With the liquid test device 10 in this embodiment, the openings 23a, 23 are created as holes on both the surface cover 19 and the retaining base 11. This embodiment is the same as the third embodiment except that the openings 23a, 23 are formed simultaneously and that the identifying parts 18a, 18b are formed by printing.

This liquid test device 10 also provides the same functional effect as the third embodiment. Furthermore, since the openings 23a, 23 on the surface cover 19 and the retaining base 11 can be formed simultaneously by boring, the liquid test device 10 can be manufactured easily.

[Modification]

Figure 13:
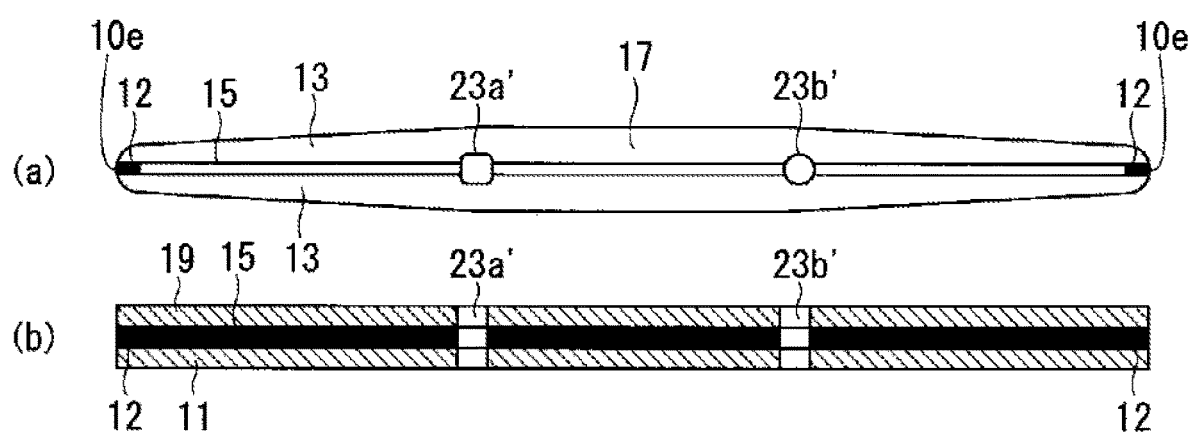
FIG. 13 shows a modification of the liquid test device according to the fourth embodiment of the present invention with the opening varied, where (a) is a front view, and (b) is a cross-sectional view in a vertical direction.
Figure 14:
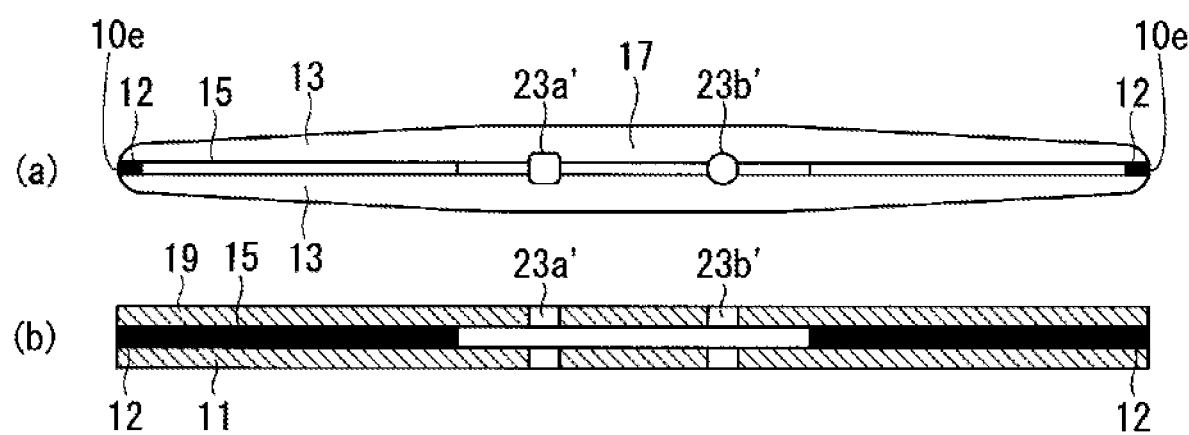
FIG. 14 shows another modification of the liquid test device according to the fourth embodiment of the present invention with the opening varied, where (a) is a front view, and (b) is a cross-sectional view in a vertical direction.

In the fourth embodiment, the openings 23a, 23b were formed smaller than the width of the liquid absorbing body 15. As shown in FIG. 13, however, they may be formed larger so that they also cover the pair of side parts. In this case, identifying parts 18a, 18b may be omitted by allowing the shapes of the openings 23a', 23b' to be different. As shown in FIG. 14, the liquid absorbing bodies 15 may also be placed separately at each end instead of continuously placing the liquid absorbing body 15 between both ends of the liquid test device 10.

In the above first to fourth embodiments, the retaining body 20 is formed into a shape whose width gradually becomes narrower from the middle position in the longitudinal direction toward the liquid contact part 10e to allow the liquid contact part 10e to easily contact a position where the liquid to be inspected such as tear meniscus is stored. However, the retaining body may be formed to have mostly constant width over its entire length (not shown).

In the above first to fourth embodiments, coloring indicators 12 are formed at the ends of the liquid contact part 10e. However, by forming them at positions apart from but close to each liquid contact part 10e, the component of the coloring indicators 12 may be prevented from dispersing from the liquid contact part 10e into the liquid to be inspected.

Fifth Embodiment

Figure 15:
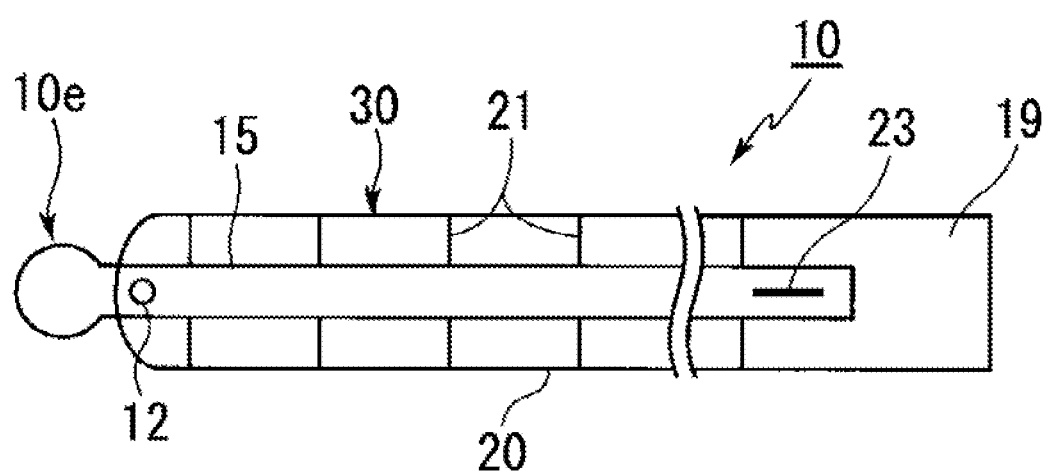
FIG. 15 is a front view showing a part of a liquid test device according to a fifth embodiment of the present invention.
Figure 16:
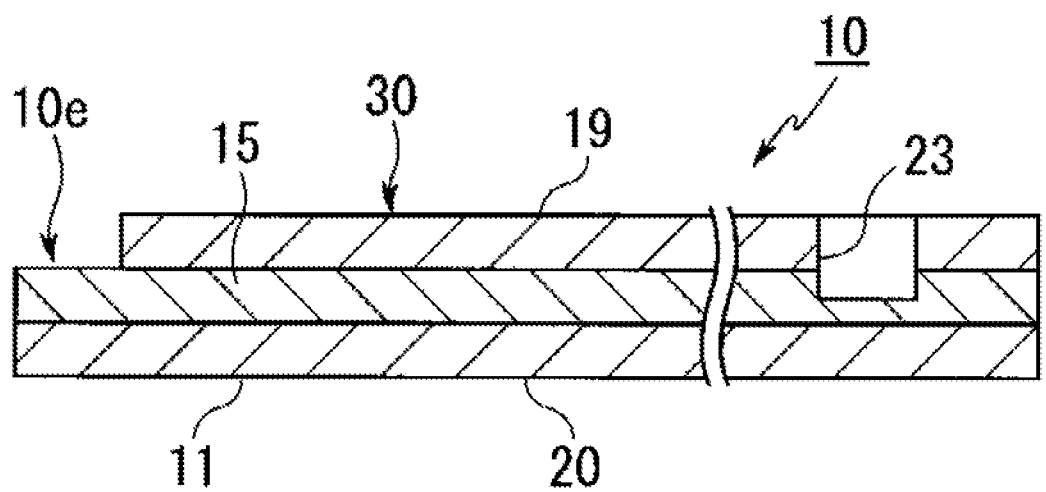
FIG. 16 is a cross-sectional view in a vertical direction of the liquid test device according to the fifth embodiment of the present invention.
Figure 17:
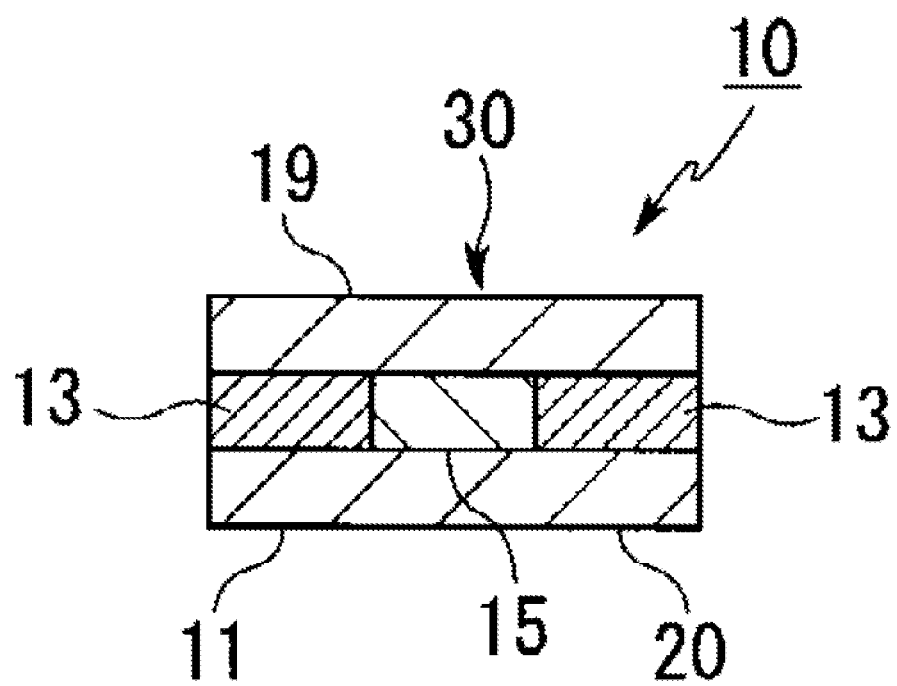
FIG. 17 is a cross-sectional view in a horizontal direction of the liquid test device according to the fifth embodiment of the present invention.

FIGS. 15 to 17 show a liquid test device in a fifth embodiment, a typical liquid test device specifically used for the inspection of dry mouth. In each figure, same symbols are assigned to the same components as those in the other embodiments. The liquid test device 10 in this embodiment has a shape of a thin plate extending along an axial direction. This liquid test device 10 includes a band-shaped main body 30 and a liquid contact part 10e protruding from an end of the main body 30 in the longitudinal direction.

In this liquid test device 10, a liquid absorbing body 15 is continuously placed from the liquid contact part 10e up to the main body 30, and this liquid absorbing body 15 is retained by a hydrophobic retaining body 20 having predetermined width and thickness. The liquid absorbing body 15 is formed in a shape of a band having mostly constant width and thickness in the main body 30. At the liquid contact part 10e, the band shape is formed wider than that in the main body 30.

The retaining body 20 has hydrophobic property, cylindrically retains the liquid absorbing body 15 in the main body 30, and constitutes the outline of the main body 30. The retaining body 20 in the main body 30 includes: a retaining base 11, which has the liquid absorbing body 15 fastened to one of its faces; side parts 13 positioned on left and right sides of the liquid absorbing body 15 so that they contact the liquid absorbing body 15 over their entire length and fastened to the surface of the retaining base 11; and a surface cover 19 that covers the surface of the side parts 13. The retaining base 11, surface cover 19, and the pair of side parts 13 are mostly adhered tightly to the liquid absorbing body 15 positioned in the main body 30 over their respective lengths.

The retaining base 11, side parts 13, and the surface cover 19 are made of a sheet or film of a hydrophobic material, a tape to one of whose faces an adhesive is attached, etc. They are made of the same or different materials. It is desirable that the side parts 13 be provided with various bases of measurement, such as a scale and color sample to be used when a liquid is absorbed. It is desirable that the surface cover 19 at least have transparency sufficient to allow the liquid absorbed by the liquid absorbing body 15 and the basis of measurement to be visible from outside.

The liquid contact part 10e in this embodiment is formed in a mostly circular or elliptical shape, and its edge at an end has a curved shape. The liquid absorbing body 15 having the liquid contact part 10e at an end is fastened to and retained by the retaining base 11 of the retaining body 20, which is formed continuously from the main body 30, on one surface, and the liquid contact part 10e is exposed to outside.

At a position apart from the liquid contact part 10e of the main body 30, an opening 23 that allows the liquid absorbing body 15 to communicate with outside is provided. The opening 23 is a cut formed on the other end of the liquid absorbing body 15.

To the liquid absorbing body 15 or the retaining body 20 that contacts the liquid absorbing body 15, a coloring indicator 12, such as the one that changes the color of the liquid absorbing body 15 by contacting the liquid to be inspected and a dissolvable coloring material, is provided to facilitate visual recognition of the liquid absorbed by the liquid absorbing body 15 or liquid interface, thereby measuring the property of the liquid. In this case, the blue No. 1 (brilliant blue FCF) is attached to and infiltrated into the surface of the liquid absorbing body 15 at a position near the end of the main body 30 and apart from the liquid contact part 10e.

The method of measuring a liquid to be inspected using the above liquid test device 10 will then be described. In this embodiment, the amount of saliva under a tongue in a mouth is measured. First, the main body 20 of the liquid test device 10 is held, the liquid contact part 10e is placed under the tongue in the mouth of a subject so that it contacts the subject's saliva to allow the saliva to contact the liquid absorbing body 15 in the liquid contact part 10e. The saliva is then absorbed by the liquid absorbing body 15 by capillary action.

When the absorbed saliva contacts the coloring indicator 12, the coloring material of the coloring indicator 12 dissolves, transfers together with the saliva, and the measurement is completed when a predetermined time has elapsed. To where the liquid interface of the liquid absorbing body 15 has reached is visually checked from the front side through the surface cover 19, and by checking the scale 21, the amount of saliva is measured. Also by using a color sample, the change in color of the liquid absorbing body 15 is checked to inspect the saliva.

The liquid test device 10 described above also provides the same functional effect as the embodiment described previously. For example, since the liquid contact part 10e is exposed from the retaining body 20 and the liquid absorbing body 15 is cylindrically surrounded by the retaining body 20 in the main body 30, fingers are not allowed to directly contact the liquid absorbing body 15. The oil or dust is not allowed to attach to the liquid absorbing body 15, thereby inhibiting absorption of the liquid to be inspected. In addition, since the liquid absorbing body 15 is cylindrically surrounded by the hydrophobic retaining body 20, the liquid absorbed does not attach to the surface of the liquid absorbing body 15 excessively, or the liquid absorbing body 15 that has absorbed the liquid does not swell excessively. Inspections can thus be performed with high accuracy. Furthermore, since the liquid absorbing body 15 is cylindrically surrounded by the hydrophobic retaining body 20, and the thickness and the width of the liquid absorbing body 15 are maintained mostly constant along the longitudinal direction, the liquid level can be displaced with accuracy in proportion to the amount of absorbed liquid. Inspection accuracy can thus be improved. In addition, since the absorbing body communicates with outside via the opening 23 at a position apart from the liquid contact part 10e of the main body 30, the air existing inside can be discharged from the opening 23 easily when the liquid absorbing body 15 absorbs the liquid. The decrease in absorption speed due to air existing within the liquid absorbing body 15 can thus be prevented, and inspection time can be shortened.

In particular, according to the liquid test device 10 in the fifth embodiment, since the liquid contact part 10e protrudes from the main body 30, it is allowed to contact the liquid to be inspected easily, and thus the liquid absorbing body 15 can be exposed in a wider range, compared to the end of the main body 30. Consequently, the contact area with the liquid to be inspected can be made wide, the resistance of absorption of the liquid to be inspected can be made small, and thus even a highly viscous liquid, etc. can be measured at sufficient absorption speed, which minimizes inspection time.

With this liquid test device 10, since one face of the liquid absorbing body 15 is exposed as the liquid contact part 10e, while the other face is retained by the retaining base 11 of the retaining body 20, a wide area for contacting the liquid to be inspected can be ensured. Furthermore, when the liquid absorbing body 15 absorbs the liquid and becomes wet, it can be maintained by the retaining body 20. Even if the elasticity, strength, etc. of the liquid absorbing body 15 decreases as a result of absorption, the liquid contact part 10e is thus prevented from being damaged or deformed, and the area of the liquid contact part 10e contacting the liquid can be maintained.

Sixth Embodiment

Figure 18:
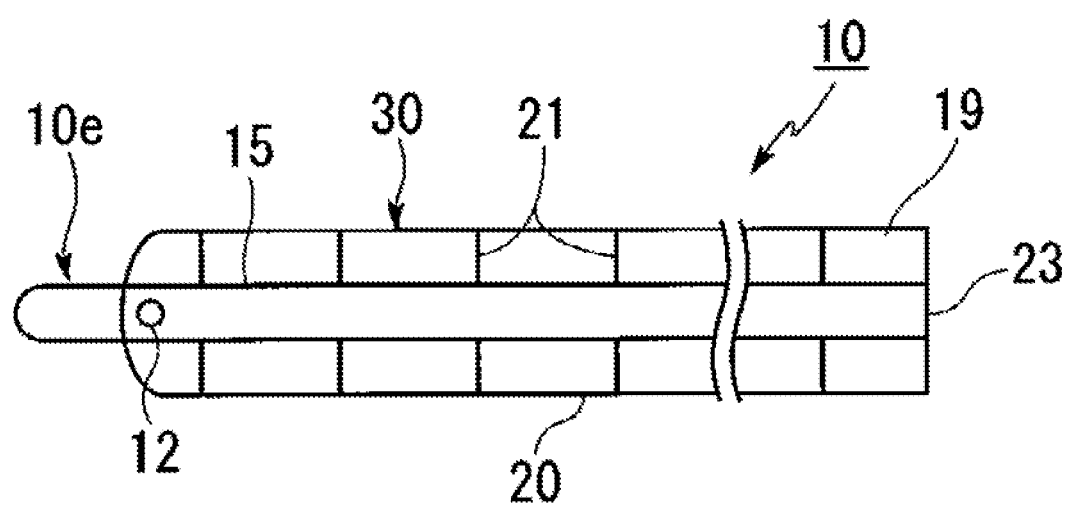
FIG. 18 is a front view showing a part of a liquid test device according to a sixth embodiment of the present invention.
Figure 19:
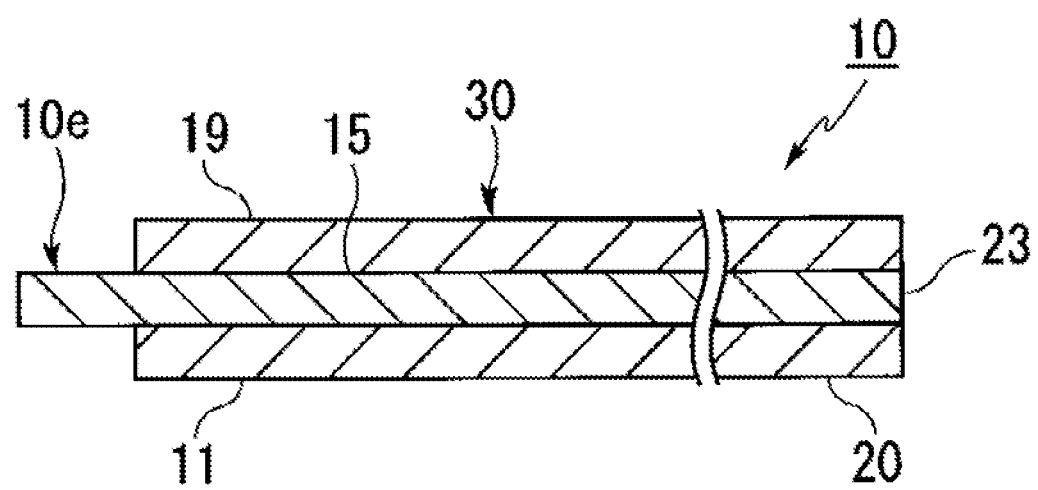
FIG. 19 is a cross-sectional view in a vertical direction of the liquid test device according to the sixth embodiment of the present invention.

FIGS. 18 and 19 show a liquid test device in a sixth embodiment. This liquid test device is used to inspect dry mouth. The sixth embodiment is the same as the fifth embodiment except that the structure of the liquid contact part 10e and the opening 23 provided in the main body 30 are different.

The liquid contact part 10e in the sixth embodiment is formed only by a liquid absorbing body 15 without a retaining body 20, and its surface, edges and rear face are exposed to outside. This liquid contact part 10e protrudes in the same width as the liquid absorbing body 15 placed in a main body 30, and its end is formed in a shape of a semicircle. The liquid absorbing body 15 is cylindrically surrounded by the retaining body 20 over the entire length of the main body 30. The end of the liquid absorbing body 15 opposite to the liquid contact part 10e is exposed to outside in a state cylindrically surrounded by the end of the retaining body 20, thereby forming an opening 23.

The liquid test device 10 in this embodiment also provides the same functional effect as the fifth embodiment. Furthermore, since the front and back faces and all the edges of the liquid contact part 10e are exposed to outside in the sixth embodiment, a liquid to be inspected can be absorbed easily by the liquid contact part 10e at the time of inspection. In addition, the liquid contact part 10e can be formed soft to minimize a sense of discomfort that is felt when it is made to contact a mouth cavity.

[Modification]

Figure 20:
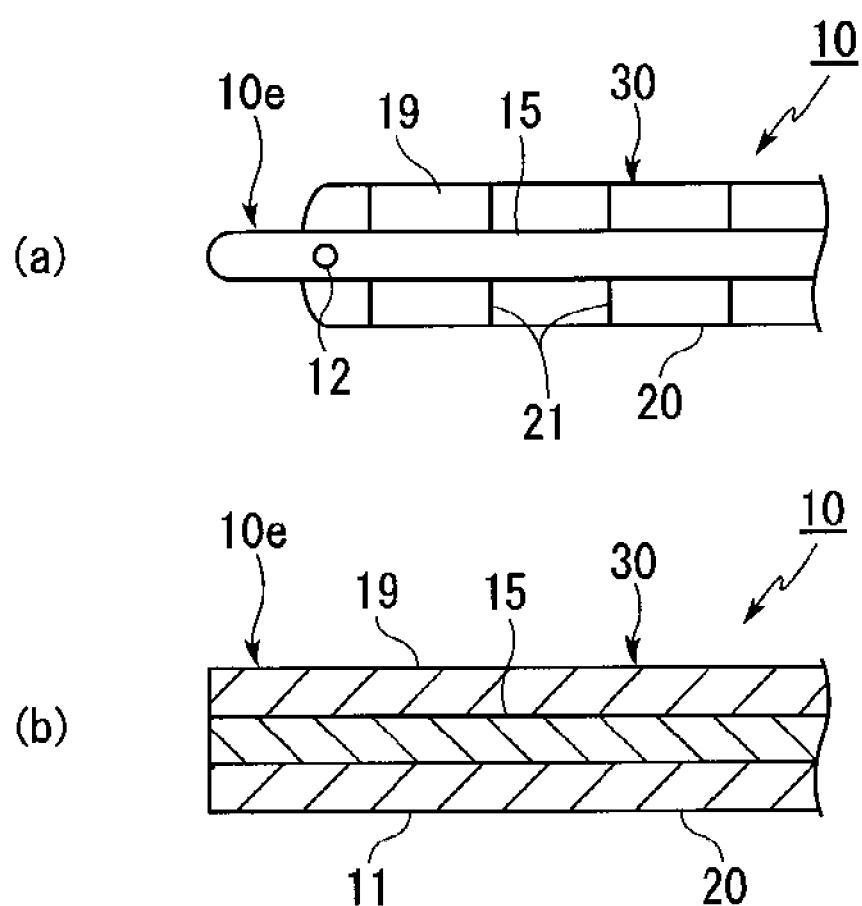
FIG. 20 (a) is a front view showing a part of the liquid test device according to a modification of the sixth embodiment of the present invention, and (b) is a cross-sectional view in a vertical direction.

FIGS. 20 (a) and (b) show modifications of the sixth embodiment. To the front and back faces of the liquid contact part 10e, a retaining base 11 and a surface cover 19 are adhered tightly as covers, but the left and right sides are exposed without being covered by side parts 13. These modifications are the same as the sixth embodiment except that the area of the exposed liquid absorbing body 15 may be twice the cross-sectional area or more of the liquid absorbing body 15 orthogonal to the longitudinal direction of the liquid absorbing body 15.

This liquid absorbing body 10 also provides the same functional effect as the fifth embodiment. Furthermore, since the front and back faces of the liquid absorbing body 15 in the liquid contact part 10e are retained by the retaining base 11 and the surface cover 19, sufficient strength can be ensured when the liquid absorbing body 15 absorbs the liquid at the time of inspection. The liquid contact part 10e can thus be prevented from being damaged or deformed, and the operation at the time of inspection is easy.

The first to the sixth embodiments described above can be modified as required within the scope of the present invention. It is also possible to apply each embodiment and its modifications to other embodiments.

Example

The present invention will hereinafter be described more in detail by referring to specific examples.

Two or more liquid test devices 10 having the liquid absorbing body 15, and the retaining body 20 including a retaining base 11, side parts 13, and a surface cover 19, both ends of the liquid absorbing body 15 being exposed as the liquid contact part 10e and the opening 23 formed as the cut and thus communicating with outside, were produced. A plastic film tape/acrylic adhesive was used for the retaining base 11, a urethane sheet was used for the side parts 13, and a urethane film tape/acrylic adhesive was used for the surface cover 19. As the liquid absorbing body 15, a rayon/pulp composite non-woven fabric having width of 0.9 mm, thickness of 0.4 mm, length of 27 mm, weighing capacity of 40 g/m$^2$, and density of 0.1 g/cm$^3$ was used.

Arc-shaped grooves having mostly V-shaped cross section were formed on the acrylic resin material as storages, and 0.16 µL to 2 µL of artificial tear was stored in each storage as liquid to be inspected. The liquid contact part 10e of the liquid test device 10 was made to contact the liquid to be inspected stored in the storage, and the liquid level was measured after 5 seconds. The results obtained are shown in the chart in FIG. 21.

Figure 21:
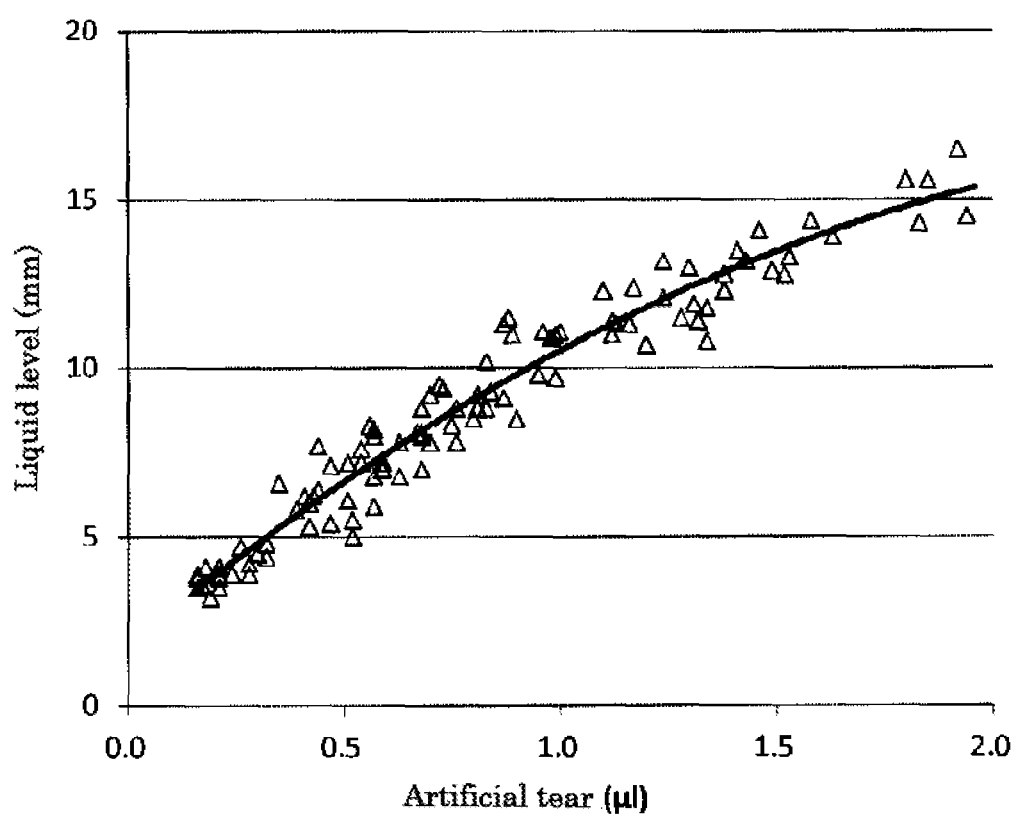
FIG. 21 is a chart showing the result of measurement taken by storing artificial tear liquid in a groove provided on an acrylic resin material in an example.

As apparent from the chart in FIG. 21, by making the liquid contact part 10e contact the liquid to be inspected, the liquid level was allowed to increase to a level where comparison was possible in 5 seconds. Furthermore, the liquid level immediately after 5 seconds of contact was found to produce high correlation with the amount of the liquid inspected.

REFERENCE SIGNS LIST

10: Liquid test device
10e: Liquid contact part
11: Retaining base
12: Coloring indicator
13: Side parts
15: Liquid absorbing body
17: Isolating part
18a, 18b, 18a', 18b': Identifying part
19: Surface cover
20: Retaining body
21: Scale
23, 23a, 23b, 23a', 23b': Opening
30: Main body

What is claimed is:

1. A liquid test device for tear meniscus, comprising: a liquid absorbing body; and a hydrophobic retaining body for retaining the liquid absorbing body by adhering to and cylindrically surrounding the periphery of the liquid absorbing body, wherein
   the liquid absorbing body is formed in a shape of a band having predetermined thickness and width,
   the retaining body comprises:
      a retaining base covering one face of the liquid absorbing body;
      side parts, that are fastened to the retaining base, covering both width sides of the liquid absorbing body;
      and a surface cover, that is fastened to the retaining base covering the other face of the liquid absorbing body,
   an entire periphery of the liquid absorbing body is adhered tightly such that no gap occurs between the liquid absorbing body and the retaining base, the surface cover, and the side parts covering both width sides of the liquid absorbing body, the liquid absorbing body is fastened by sandwiching the liquid absorbing body between the retaining base and the surface cover, and the thickness of the liquid absorbing body is being compressed to be a same thickness as the side parts,
   a liquid contact part is provided at an end of the retaining body by exposing an end of the liquid absorbing body,
   an opening for allowing an other end of the liquid absorbing body to communicate with outside is provided at a position of the retaining body or the surface cover, or of both, apart from the liquid contact part and at a position corresponding to the other end of the liquid absorbing body,
   the liquid absorbing body, other than the liquid contact part and the opening, is not exposed to outside air,
   a material for the liquid absorbing body is selected from any one of resins, fibers including rayon or pulp, woven cloth, nonwoven cloth or paper, and a scale for measuring the amount of liquid absorbed by the liquid absorbing body is provided between the liquid contact part and the opening, and wherein when a tear is made to contact the liquid contact part, and the tear is absorbed by the liquid absorbing body, air existing within the liquid absorbing body is discharged from the opening, and the liquid absorbing body has an absorbing speed of 3 mm/sec to 30 mm/sec when the liquid absorbing body is immersed in a stored liquid to be inspected for 5 seconds in a vertical direction, and wherein the opening is a cut or a port formed at a position of the retaining body or the surface cover, or of both, corresponding to the liquid absorbing body.

2. The liquid test device for tear meniscus as set forth in claim 1, comprising: a band-shaped main body having the liquid absorbing body and the retaining body; and the liquid contact part protruding from one end of the main body, thereby exposing the liquid absorbing body to outside of the main body.

3. The liquid test device for tear meniscus as set forth in claim 2, wherein one face or both faces of the liquid contact part is/are retained by the retaining base of the retaining body or the surface cover.

4. The liquid test device for tear meniscus as set forth in claim 1, wherein a plurality of the liquid absorbing bodies are provided via an isolating part of the retaining body, and the plurality of the liquid absorbing bodies are respectively exposed at the different liquid contact parts.

5. The liquid test device for tear meniscus as set forth in claim 1, wherein a coloring indicator made of a dissolvable or dispersible dye depending on the liquid to be inspected is provided on the end of the liquid absorbing body provided upon an end of the liquid contact part.

6. The liquid test device for tear meniscus as set forth in claim 1, wherein the entire liquid absorbing body is impregnated with a pH indicator.

7. The liquid test device for tear meniscus as set forth in claim 1, wherein as the material for the liquid absorbing body, a weighing capacity is ranged from 30 g/m$^2$ to 100 g/m$^2$, or a density is ranged from 0.05 g/cm$^3$ to 0.3 g/cm$^3$.

8. A liquid test device for tear meniscus, comprising: a liquid absorbing body; and a hydrophobic retaining body for retaining the liquid absorbing body by adhering to and cylindrically surrounding the periphery of the liquid absorbing body, wherein the liquid absorbing body is formed in a shape of a band having predetermined thickness and width, the retaining body comprises:

a retaining base covering one face of the liquid absorbing body;

side parts, that are fastened to the retaining base, covering both width sides of the liquid absorbing body;

and a surface cover, that is fastened to the retaining base covering the other face of the liquid absorbing body, an entire periphery of the liquid absorbing body is adhered tightly such that no gap occurs between the liquid absorbing body and the retaining base, the surface cover, and the side parts covering both width sides of the liquid absorbing body, the liquid absorbing body is fastened by sandwiching the liquid absorbing body between the retaining base and the surface cover, and the thickness of the liquid absorbing body is being compressed to be a same thickness as the side parts, a liquid contact part is provided at an end of the retaining body by exposing an end of the liquid absorbing body, an opening for allowing an other end of the liquid absorbing body to communicate with outside is provided at a position of the retaining body or the surface cover, or of both, apart from the liquid contact part and at a position corresponding to the other end of the liquid absorbing body, the liquid absorbing body, other than the liquid contact part and the opening, is not exposed to outside air, a material for the liquid absorbing body is selected from any one of resins, fibers including rayon or pulp, woven cloth, nonwoven cloth or paper, and a scale for measuring the amount of liquid absorbed by the liquid absorbing body is provided between the liquid contact part and the opening, wherein two of the liquid absorbing bodies are provided via an isolating part of the retaining body, and two of the liquid absorbing bodies are respectively exposed at the different liquid contact parts, wherein when a tear is made to contact the liquid contact part, and the tear is absorbed by the liquid absorbing body, air existing within the liquid absorbing body is discharged from the opening, and the liquid absorbing body has an absorbing speed of 3 mm/sec to 30 mm/sec when the liquid absorbing body is immersed in a stored liquid to be inspected for 5 seconds in a vertical direction, wherein the opening is a cut or a port formed at a position of the retaining body or the surface cover, or of both, corresponding to the liquid absorbing body, and wherein the liquid contact part is provided at both ends of the retaining body in a longitudinal direction, and an identifying part for allowing the liquid contact part provided at said both ends of the retaining body to correspond to inspection targets provided at said both ends of the retaining body.

9. The liquid test device for tear meniscus as set forth in claim 8, comprising: a band-shaped main body having the liquid absorbing body and the retaining body; and the liquid contact part protruding from one end of the main body, thereby exposing the liquid absorbing body to outside of the main body.

10. The liquid test device for tear meniscus as set forth in claim 9, wherein one face or both faces of the liquid contact part is/are retained by the retaining base of the retaining body or the surface cover.

11. The liquid test device for tear meniscus as set forth in claim 8, wherein a coloring indicator made of a dissolvable or dispersible dye depending on the liquid to be inspected is provided on the end of the liquid absorbing body provided upon an end of the liquid contact part.

12. The liquid test device for tear meniscus as set forth in claim 8, wherein the entire liquid absorbing body is impregnated with a pH indicator.

13. The liquid test device for tear meniscus as set forth in claim 8, wherein as the material for the liquid absorbing body, a weighing capacity is ranged from 30 g/m$^2$ to 100 g/m$^2$, or a density is ranged from 0.05 g/cm$^3$ to 0.3 g/cm$^3$.

* * * * *